United States Patent [19]

Byrne et al.

[11] 4,406,883

[45] Sep. 27, 1983

[54] CONTROLLED RELEASE SUPPOSITORIES CONSISTING ESSENTIALLY OF A LINEAR POLYMER PARTICULARLY, POLYVINYL PYRROLIDONES

[75] Inventors: Geoffry A. Byrne, Gifford; Ross I. Aylott, Edinburgh, both of Scotland

[73] Assignee: Merrell Dow Pharmaceuticals Inc., Cincinnati, Ohio

[21] Appl. No.: 248,475

[22] Filed: Mar. 27, 1981

Related U.S. Application Data

[63] Continuation-in-part of Ser. No. 817,412, Jul. 20, 1977, Pat. No. 4,292,300.

[51] Int. Cl.³ .................. A61K 9/02; A61K 9/22; A61K 31/79
[52] U.S. Cl. ................... 424/80; 424/14; 424/19; 424/22
[58] Field of Search .............. 252/316; 260/29.6 B, 260/29.6 HN; 424/DIG. 15, 78, 80, 81, 361, 362, 358

[56] References Cited

U.S. PATENT DOCUMENTS

| | | | |
|---|---|---|---|
| 2,571,706 | 10/1951 | Sargent | 260/29.6 B |
| 2,580,362 | 12/1951 | Sargent | 260/29.6 B |
| 2,646,411 | 7/1953 | Sargent et al. | 260/29.6 B |
| 2,658,045 | 11/1953 | Schildknecht | 252/316 |
| 2,726,982 | 12/1955 | Ochs et al. | 424/362 |
| 3,443,563 | 5/1969 | Ishihama et al. | 424/DIG. 15 |
| 3,939,099 | 2/1976 | Tusa et al. | 252/316 |
| 3,964,832 | 6/1976 | Cohen et al. | 252/316 |
| 4,024,073 | 5/1977 | Shimizu et al. | 252/316 |
| 4,071,616 | 1/1978 | Bloch | 252/316 |
| 4,265,875 | 5/1981 | Byrne et al. | 424/362 |
| 4,292,300 | 9/1981 | Byrne et al. | 424/362 |

*Primary Examiner*—Shep K. Rose
*Attorney, Agent, or Firm*—McAulay, Fields, Fisher, Goldstein & Nissen

[57] ABSTRACT

A slow-release suppository is provided. The slow-release suppository comprises a linear polymer, water and a therapeutically active ingredient. In particular, in accordance with the present invention, the linear polymer can be a polyvinyl alcohol, a polyvinyl pyrrolidone, a polyacrylamide, a chemically modified starch, or a combination of these materials.

7 Claims, 13 Drawing Figures

ULTRAVIOLET SPECTROSCOPIC DATA ON LIGNOCAINE HYDROCHLORIDE IN WATER

RELEASE OF LIGNOCAINE HYDROCHLORIDE FROM HYDROXYPROPYL METHYL CELLULOSE SUPPOSITORIES

CURVE A: 56 mg DRUG + 470 mg POLYMER (i.e. 10.6 % DRUG)
CURVE B: 112 mg DRUG + 940 mg POLYMER (i.e. 10.6 % DRUG)

FIGURES IN BOXES SHOW AMOUNT OF DRUG RELEASED.

MEAN PLASMA CONCENTRATION OF $(^{14}C)$-LIGNOCAINE HCl
EXPRESSED AS PERCENTAGE OF THE TOTAL DOSE /ml
("AGED" SUPPOSITORIES)

CONTROLLED RELEASE SUPPOSITORIES CONSISTING ESSENTIALLY OF A LINEAR POLYMER PARTICULARLY, POLYVINYL PYRROLIDONES

This application is a continuation-in-part of our copending application Ser. No. 817,412 filed July 20, 1977 for "Controlled Release Suppositories," now U.S. Pat. No. 4,292,300, assigned to the same assignee as the present invention. Also copending with this application is application Ser. No. 086,471 filed Oct. 19, 1979 for "Controlled Release Suppositories," now U.S. Pat. No. 4,265,875, assigned to the same assignee as the present invention both based upon prior United Kingdom application Nos. 30793/76 of July 23, 1976 and 30793/76 filed Oct. 24, 1977, the priority of which are claimed herein.

The present invention relates to slow-release suppositories containing therapeutically active ingredients.

Conventional suppositories usually contain either hydrophobic or hydrophilic media, both of which normally melt at body temperature. The hydrophobic media used such as cocoa butter, have certain disadvantages. They can become rancid, they can melt in warm weather, they can liquefy when incorporated with certain therapeutic agents and they can isomerise to give a product with an unacceptably low melting point. The hydrophobic and hydrophilic media used can melt to form a fluid which is inconvenient to the user.

British Pat. No. 1,070,492, in the name of Richardson Merrell, describes the use of hydroxypropylmethyl cellulose and ethyl cellulose in the absence of added water to form sustained release tablets. British Pat. No. 1,171,691, discloses a product based on the above mentioned two polymers with undefined amounts of water, the water being added by a 'humidification' process which is different from our current method of adding liquid water.

The method for adding water described in Forest Laboratory's British Pat. No. 1,279,214 and U.S. Pat. No. 3,870,790 is quite specific, viz. the solid particulate polymer is exposed to water vapour (not liquid water) until a particular moisture content is achieved. This process is very time consuming, 24 to 36 hours being usual. The desired water content is then achieved by heating the moist polymer with hot air (up to 12 hours). This process precludes the incorporation of many drugs which are thermally unstable. Hence, the cooled, moist polymer is then mixed with the active ingredient and compressed into the desired form.

Neither of these patents describes a method whereby the polymer(s) is mixed with liquid water or with liquid water containing the active ingredient. The process of the present invention is simpler and quicker.

British Pat. No. 1,279,214 states on Page 1 lines 58 to 65 that "The present invention relates to a shaped compressed product adapted to be retained in the mouth for buccal or sublingual administration and is concerned with an improvement of the invention disclosed in our Specification No. 1,171,691, in that the present invention stipulates the necessity to use a specific amount of water". Neither of the Forest patents discloses products with more than about 25% water. It is thought that the humidification process does not easily give a product with more than about 25% water; and even if it was obtained, the resultant product may have poor mechanical properties when made by a compression process or may have inadequate drug release properties.

The products of the Forest Laboratory Patents are made by a process of low compression (5 to 8 lbs/sq. inch) or somewhat higher compression (up to about 30 lbs/sq. inch). While we have no reason to doubt the performance of products made at these pressures from material prepared by the humidification process, we have shown in our own work (set out later in our specification) that such low compression does not yield satisfactory suppository products containing 30% water (or, by implication, less than 30% water).

The Forest patents clearly state that the mechanism for lozenges (and, by implication, for suppositories), is one of dissolution and/or disintegration of the whole product. We have shown experimentally that our suppository does not dissolve or disintegrate in vivo, and claim a mechanism of diffusion of drug through the 'bound' water, and suggest that such diffusion would be limited or virtually non-existent in products containing 25% water or less and made by our extrusion method.

The present invention provides a slow-release suppository consisting essentially of a linear polymer, water and a therapeutically effective amount of a water-soluble therapeutically active ingredient wherein the water is present in an amount of more than 35 parts by weight, and less than 65 parts by weight of linear polymer. The slow-release suppository preferably contains about 35 to about 70 parts by weight of water and about 30 to about 65 parts by weight of linear polymer; more preferably about 40 to about 70 parts by weight of water and about 30 to about 60 parts by weight of linear polymer and most preferably about 50 parts by weight of water and 50 parts by weight of linear polymer.

In general the mechanical properties of suppositories containing between about 35 and about 40 parts by weight of water are not so good as the mechanical properties of suppositories containing about 50 parts by weight of water.

The suppository of the present invention does not melt in the body nor are significant quantities of water lost to the body and the suppository is evacuated in essentially its original form.

The suppository of the present invention may be prepared by the following general method. The therapeutically active ingredient is dissolved in water and the resulting solution is added to the polymer with thorough mixing to ensure that the therapeutically active ingredient is homogenously distributed. The resulting mixture is extruded at ambient temperature and the extruded material is cut into short lengths, i.e., suppositories. If desired, the resulting suppositories can be wrapped in a protective material such as aluminum to prevent loss of water.

In a preferred embodiment a suppository weighing about 2 g is made of equal parts of a polymeric cellulose ether (Methocel E 50 Premium, a hydroxypropylmethylcellulose) and water containing additional small quantities of a drug or drugs.

A formation mix is prepared by dissolving the required quantity of drug in water, adding this solution to the polymer and thoroughly mixing by hand or by machine (e.g., a Z-blade mixer). The solution and polymer should be sufficiently well mixed to achieve homogeneous distribution of the drug throughout the mix since, otherwise, reproducible drug release rates cannot be guaranteed. The suppositories may be made for example by a simple process of extrusion at ambient temperature.

In laboratory experiments, the damp dough is extruded into a long rod (~9 mm diameter) by forcing the dough through a widened nozzle of a plastic syringe. In process operations, an extruder normally used for plastic extrusion is used, if necessary after adaption. The long rod is cut up into shorter lengths, i.e. into suppositories. Although at present, we prefer to use extrusion, we may alternatively use injection moulding or transfer moulding.

The polymers used in the present invention are linear polymers and are to be distinguished from cross-linked polymers which swell, but do not dissolve in the presence of water and certain organic solvents. The polymers of choice have the following characteristics; they have a high molecular weight (so minimizing the possibility of adsorption of low molecular weight fractions by the body) and an affinity for water (although the polymers will themselves dissolve in excess water, in the relatively small amounts of water used in the formulation, a "gel"-like mass is formed). They are chemically inert. Preferably they resist biodegradation or are only slowly biodegradable. They are compatible with a wide range of therapeutically active ingredients and they are capable of being extruded at ambient or near ambient temperatures, e.g. 15° C. to 40° C. to give products with good strength and elasticity. They also have the ability to become instantaneously slippery when only slightly moistened and are therefore easily inserted into the anorectal or vaginal passage; this property is enhanced by the presence of the relatively large amounts of water in our formulations.

Examples of linear polymers which can be used in the present invention include methylcellulose, hydroxypropylmethylcellulose, hydroxymethylcellulose, polyvinyl alcohols, polyvinyl pyrrolidones, polyacrylamides, and certain modified starches. Typical average molecular weights vary between 100,000 and 400,000. Since water solubility decreased with average molecular weight, it is possible to use different molecular species to obtain suppositories of similar mechanical and release properties but with different water contents. The handling properties of the drug containing films can be modified by the addition of a water soluble plasticiser (glycerol). Our afore-referenced application Ser. No. 817,412 describes the same materials, but claims only methylcellulose for the suppositories of the present invention, while my afore-referenced application Ser. No. 086,471 while describing the same materials, claims only the hydroxyproplymethylcellulose linear polymer.

The therapeutically active ingredient incorporated in the suppository of the present invention must be water soluble. Examples of therapeutically active ingredients which can be incorporated into the suppositories of the present invention are lignocaine hydrochloride, phenylephrine hydrochloride, betamethasone sodium phosphate, sodium prednisolone metasulphobensoate, disodium prednisolone phosphate, methyl prednisolone sodium succinate, dexamethasone sodium phosphate and hydrocortisone sodium phosphate.

The rate of release of lignocaine hydrochloride for example from the suppositories can be varied by varying the total amount of drug in the suppository and also by varying the ratio of drug to polymer.

Both in vitro and in vivo tests were carried out. In the initial series, the in vitro tests showed that 50% of available drug was released within 30-90 mins (depending on formulation) and 80% of available drug was released within 3 to 5 hours. A somewhat slower release rate was forecast for in vivo situations.

The following experimental procedure was adopted for the in vitro tests

I Initial in vitro tests

General Procedure: Development of in vitro test

Polymer suppositories were made and evaluated in the following way.

A known amount of drug was dissolved in an aqueous solution of polymer. The solution was spread onto a glass plate and allowed to dry. The dry film containing some water was removed from the plate, cut to a required size, and wrapped around a semi-rigid polythene rod former. The end of the film was sealed by slight moistening with water.

The swelling behavior of the film was observed visually and by measuring the increase in weight when it was immersed in water at 37° C.

Drug release rates were determined in vitro by suspending the suppository in a beaker of water at 37° C. and periodically analysing the water for drug by a spectrophotometric method.

Materials

Drug

It was proposed to study the release behaviour of two drugs, viz, lignocaine hydrochloride (as local anaesthetic) and phenylephrine hydrochloride (as local vasoconstrictor). However, our early work was done with lignocaine hydrochloride, only.

It was anticipated however and later confirmed that the release rates of both drugs would be similar.

Polymer (i) Methyl cellulose (ex BDH); degree of methoxyl substitution 53% viscosity of 2% solution in water at 20° C. = 350–550 cP.

(ii) Methofas PM 1500 (hydroxpropyl methyl cellulose, ex ICI); degree of methoxyl substitution 27–30% viscosity of 2% solution in water at 20° C. = 1500 cP$\pm$300 cP; molecular weight ~125,000.

Both polymers can be obtained in a number of grades differing in molecular weight, degree of substitution, water solubility, and water swellability. They are excellent film formers and their strength, flexibility and water absorption properties (and subsequent drug release behaviour) can be modified by the addition of plasticisers (e.g. hydrophilic materials such as glycerol to aid water absorption). Both polymers have a record to date of nontoxicity in the food and drug industries.

Preparation of Polymer Films

The following procedure, with occasional slight variations, was adopted for the production of drug-containing polymer films.

Unplasticised Films

Lignocaine hydrocaine hydrochloride (720 mg or as described in text) was dissolved in distilled water (400 ml) at 70° C. and powdered polymer, (10 g) added with stirring. Stirring was continued for about 1 h at 70° C. and the mixture was then allowed to cool, but stirring was maintained for up to 6 h. The viscous solution, on standing overnight, yielded a smooth clear gel.

Films (0.35 cm wet thickness) were cast onto clean glass plates using a conventional thin layer chromatography spreader. The wet films were heated at 60° C. until a clear film was formed.

Plasticised Films

Plasticised films containing 2% and 10% glycerol were prepared by adding the appropriate amount of glycerol to the systems prior to the addition of polymer.

Dried films were cut into strips (normally 17×4.7 cm) weighing about 1 g and wrapped around semi-rigid polythene formers (short lengths of polythene rod). This operation was done more easily if the surface of the strip was *slightly* moistened with water.

Determination of Drug Release Rate

The following procedure was adopted. The suppository was suspended in a beaker of unstirred water at 37° C. Periodically, aliquots (∼4 ml) were removed, analysed spectrophotometrically (at 263 nm), and returned to the beaker. Before removing the aliquot, the solution was stirred to ensure that a representative sample was taken.

Determination of Swelling Rate of the Films

A rough indication (see below) of the swelling properties of the films was obtained by measuring the weight change when experimental suppositories were immersed in unstirred water at 37° C.

Preparation of Films

In order to avoid the formation of air bubbles (which can subsequently appear in the dried films) during preparation of the aqueous polymer drug solution it was necessary to stir the solution with a magnetic stirrer rather than with a fastaction mechanical stirrer.

Drug Stability

It was confirmed spectrophotometrically that lignocaine hydrochloride was not degraded during prolonged (∼12 h) storage in aqueous solution at 70° C.

Handling Properties of Films

The general handling properties of films made from methyl cellulose and hydroxypropyl methyl cellulose are described below.

(i) Unplasticised film

Slightly brittle; becomes instantly slippery when moistened; layers are self-scaling when moistened; fairly easily wrapped around the former; dissolves in *excess* water after 24 h or more.

(ii) Plasticised (2% glycerol) film

Excellent casting and wrapping properties; layers are easily self-sealed on very slight moistening; very slippery when moistened; dissolves in *excess* water after 24 h or more.

(iii) Plasticised (10% glycerol) Film

Slightly better properties than the film plasticised with 2% glycerol. (It is thought that the introduction of more than 10% glycerol would cause the film to be too flexible for easy handling).

It is apparent that plasticised films exhibit the best handling properties. Their ability to become slippery on only slight moistening is an obvious advantage for in vivo application. Similar properties are obtained with films made from polyvinyl alcohols, polyvinylpyrrolidones, polyacrylamides, and chemically modified starches, in accordance with the present invention.

Swelling Behaviour

In addition to visual observation, the ease with which experimental suppositories absorb liquid water was assessed by measuring the increase in weight when drug-free suppositories were immersed in water for prolonged periods of time.

Quantitive results could only have been obtained if:

(i) The polymer was completely insoluble in water; and (ii) plasticiser was not lost to the solution.

Since the films are not completely insoluble in water and glycerol is very soluble in water, the swellability data could only be semi-quantitative.

Typical results are shown in FIG. 1 of the accompanying drawings which shows graphs of the swellability of various polymer films. The results can be summarised as follows:

(a) The presence of plasticiser (2%) in the polymer does not appear to increase water uptake (compare curves A and B)

(b) Unplasticised methyl cellulose appears to absorb water somewhat faster than does unplasticised hydroxypropyl methyl cellulose (compare curves A and C).

These results are obtained with a system containing a vast excess of water (i.e. a near perfect sink). In the anorectal canal there is likely to be much less available fluid with the result that, although we expected relatively similar effects to those in FIG. 1, we also expected that the rate of water uptake and the resulting swelling would be somewhat lower.

The above behaviour observed on a limited number of samples could well be affected by differences in film thickness and tightness of film wrapping.

Drug Release Behaviour

The laboratory method of determining drug release rates is suitable for comparing the behaviour of different experimental products. However, for the reasons mentioned above, it does not accurately represent the in vivo system where *slower* release rates than those reported here are to be expected.

Results are given in FIGS. 2, 3 and 4 of the accompanying drawings.

FIG. 2 shows the ultraviolet spectrum of lignocaine hydrochloride in water, together with the plot of absorbance versus drug concentration which shows that Beer's law is accurately obeyed up to 1 g/l lignocaine hydrochloride. Drug release data are given in FIGS. 3 and 4 of the accompanying drawings.

In FIG. 3, each curve is the average of two separate experiments in which reproducibility was very good (<±5%). Initially, it was thought that the addition of a water-soluble plasticiser (glycerol) would have a marked effect on the drug release rate. This was not the case in the laboratory in vitro system. However, it was thought that, in the ano-rectal canal, where the amount of available water is limited, the rate of drug release from a plasticised system would be greater than from an unplasticised system (plasticisation increases permeability, because, by reducing cohesive forces between polymer chains, it leads to increased diffusivity).

The difference in release rates observed with unplasticised methyl cellulose and hydroxypropyl methyl cellulose systems is thought to be due mainly to the different ratios of drug to polymer rather than to any significant difference in polymer properties.

The effect of total amount of drug thickness of suppository is shown in FIG. 4. Both suppositories were made from the same drug-containing film but suppository B contained about twice the number of wrapping turns as suppository A. At any time, a higher percentage of available drug is released from the thinner suppository (curve A). Initially, the amounts of drug lost from both suppositories are similar; as time proceeds, a greater amount of drug is released from the thicker suppository containing the higher initial amount of drug. The implications of these data are that, by varying the total amount of drug and the ratio of drug to polymer, suppositories with a wide range of release rates could be made. The total permissible amount of drug will, of course, be determined by safety and economic factors. It is emphasised that the experiments with suppositories made by the 'film' process were done with the main objective of developing a suitable in vitro release test which could be used to compare experimental products containing relatively large amounts of water and made by the extrusion process. When a suppository made by the film process is evaluated in the in vitro test (in which they are immersed in water), the suppository absorbs relatively large amounts of water (see FIG. 1) and in this state they may be considered to be similar to suppositories made by the extrusion process and containing at least 35% water.

II Further in vitro tests and in vivo tests

A. Preparation of Suppositories

Materials

Methocel E50 Premium (the Dow Chemical Company) lignocaine hydrochloride (Duncan, Flockart & Company) and phenylephrine hydrochloride (Cambrian Chemicals Ltd) were used. Deionised, doubly distilled water was used throughout.

Procedure

Extrusion Process

Mixes for the in vivo and the in vitro trails were made by dissolving the required quantities of drug in water which was then added to the polymer and thoroughly mixed using a spatula. Quantities were chosen so that each suppository should contain 20 mg. phenylephrine hydrochloride, 80 mg. lignocaine hydrochloride, 1 g. polymer and 1 g. water. The resulting damp, spongy particles were squeezed together by hand to form a dough-like mixture. The mixes were extruded through a nozzle of a 50 ml plastic syringe to form a long rod (9 mm diameter). Immediately after, suppositories were made by cutting the rod into 3 cm length and were stored in an air-tight container prior to use.

B. In Vitro Trial

Determination of Drug Release Rates

Drug release rates were studied in four ways:
(i) release from suppositories containing 20 mg phenylephrine hydrochloride only (in duplicate).
(ii) release from suppositories containing 80 mg lignocaine hydrochloride only (in duplicate).
(iii) release from suppositories containing both drugs in the above amounts (in triplicate).

Each suppository was suspended from a wire and immersed in 150 ml of water at 37° C. At set intervals, the suppository was removed, the solution stirred with a glass rod and a 4 ml aliquot removed. The concentration of drug in the aliquot was immediately determined spectrophotometrically (q.v.) after which the aliquot sample was returned to the solution. Losses due to evaporation were eliminated by making the solutions up to 150 ml before each sampling.

(iv) release from one suppository containing both drugs as at (iii) above together with a known quantity of [$^{14}$C]-lignocaine hydrochloride. The suppository was examined in the same way as described above except that 0.1 ml aliquots were removed at set intervals and assayed for radioactivity. Full experimental details are given below in Section C relating to in vivo trials.

Control Experiment

Analytical background effects (due to the polymer) were measured by repeating the spectrophotometric procedure using a suppository containing no drug.

Analysis of Drugs

Reagents

Standard phenylephrine hydrochloride solution (with concentration equivalent to 20 mg/150 ml):133.3 mg of dry phenylephrine hydrochloride were dissolved in water and diluted to 1 liter.

Standard lignocaine hydrochloride solution (80 mg/150 ml):533.3 mg of dry lignocaine hydrochloride were dissolved in water and diluted to 1 liter.

Mixed standard phenylephrine hydrochloride and lignocaine hydrochloride: The above quantities of drugs were dissolved together and diluted to 1 liter.

Ultra-violet Spectrophotometer

Spectrophotometry was conducted on a Pye Unicam SP800 in the fixed wavelength mode at 260 nm using 10 mm pathlength cells.

Procedure

1. Preparation of calibration curves see FIG. 5 of the accompanying drawings
   (i) Phenylephrine hydrochloride. Aliquots of the 20 mg/150 ml standard were diluted to produce standards containing the equivalent of 2, 4, 8, 12 and 16 mg/150 ml. A calibration curve of absorbence versus concentration was obtained.
   (ii) Lignocaine hydrochloride. Aliquots of the 80 mg/150 ml standard were diluted to give standards containing the equivalent of 8, 16, 32, 48, and 64 mg/150 ml and a similar calibration curve was obtained.
   (iii) Both drugs. Aliquots of the two working standards were diluted to give standards containing the equivalent of both 2, 4, 8, 12 and 16 mg/150 ml phenylephrine hydrochloride and 8, 16, 32, 48 and 64 mg/150 ml lignocaine hydrochloride respectively. A calibration curve of absorbence versus total concentration was obtained.

2. Analysis of Samples

The absorbences of the samples taken during the in vitro trial were measured on the spectrophotometer and the concentrations of the dissolved drugs determined by reference to the calibration curves.

C. In Vivo Trial

Materials and Methods

Preparation of Suppositories

The suppositories for the in vivo trial were made in the same way as for the in vitro work. The following mix, enough for 3 suppositories, was prepared.
3 g polymer
3 g water
60 mg phenylephrine hydrochloride 230.5 mg lignocaine hydrochloride
9.5 mg [$^{14}$C]-lignocaine hydrochloride, 100 uCi specific activity 2.85 mCi/mmole.

One suppository was used for the in vivo trial, one for an in vitro trial in which the dissolved solution was assayed for radioactivity and the remainder for the estimation of the radioactive dose.

Animal

A young adult beagle of approximately 5 kg body weight was used. This was fed on a normal laboratory diet until taken for experimentation. The dog was starved overnight before dosing and deprived of food for a further four hours after dosing. Water was available at all times.

Dosing

For the period of the experiment, the dog was kept in a stainless steel metabolism cage with facilities for the separate and quantitative collection of urine and faeces. The animal was dosed by manual insertion of the [$^{14}$C]-labelled suppository into the rectum.

Collection of Samples (i) Plasma

Samples of blood (10 ml) were withdrawn from the jugular vein into lithium heparin tubes at the following intervals, (post application):

0, 0,5, 1, 2, 4, 8, 24, 48, h.

Plasma was separated by centifuging and samples were taken for the assay of radioactivity immediately after separation.

(ii) Urine and Faeces 24 h and 48 h urine samples were collected. The cage was rinsed with approximately 500 ml distilled water after each collection and the rinse was pooled with the urine sample. Aliquots were taken for the assay or radioactivity immediately after collection. A single collection of faeces were made over the study.

(iii) Tissues

After the collection of the 48 h pooled sample, the dog was killed by the intravenous injection of Expiral (sodium pentobarbitone). After exsanguination, the following tissue/fluid was removed:

Liver, rectrum, rectal contents, bile.

The contents of the bladder were removed and included with the urine sample. The tissue/fluids were stored at −20° C. prior to analysis.

Measurement of Radioactivity

Radioactivity was measured using either an Automatic Liquid Scintillation Analyser (Philips, N.V., Holland), coupled to a Data Dynamics 390 print-out, or an LS100 liquid scintillation counter (Beckman Instruments Ltd., Glenrothes, Fife). Quench correction in both cases was by the external standard-channels' ratio method. This was automatically performed on the Philips instrument whereas cpm (counts per minute) data from the Beckman instrument were converted to dpm (disintegratitons per minute) by reference to quench curves. Counting efficiencies in all cases were greater than 85%. Samples were counted to a preset ±2 $\sigma$ error of 1% (equivalent to $10^4$ cpm).

All samples of plasma, bile and urine were measured in duplicate while faecal and tissue homogenates were measured in triplicate. Estimation of the radioactivity present before and after the experiment was performed in quadruplicate. All values quoted are means of the multiple determinations.

(i) Plasma, Bile and Urine

Aliquots of the above fluids (0.5 ml plasma, 0.1 ml bile, 1.0 ml urine) were made up with distilled water to a final volume of 1.0 ml, and were mixed with Unisolve 1 (10 ml, KochLight Laboratories Ltd.), a xylene/nonionic detergent based scintillation fluid. The samples were allowed to stabilise in the dark for 8H prior to scintillation counting.

(ii) Faecal and tissue Homogenates

All samples of tissues and faeces were homogenised in the minimum volume of water; the homogenates being stabilised by the addition of sodium carboxymethyl cellulose.

Weighed aliquots were combusted using an Oxymat automatic sample oxidiser (Intertechnique Ltd). The resulting $^{14}CO_2$ was absorbed in a $\beta$-phenylethylamine-based scintillator for measurement of radioactivity.

The routine combustion of radioactive standards indicated a consistent combustion efficiency of 98% which has been compensated for in all calculations.

(iii) Estimation of Radioactive Dose

After extrusion of a quantity of [$^{14}$C]-labelled material, the suppository for administration was cut off and weighed. Four smaller pieces were randomly cut from the remainder and placed into weighed vials. Distilled water (10 ml) was added to each vial and the contents were allowed to dissolve overnight. Triplicate aliquots (0.1 ml) were removed for the determination of radioactivity as for plasma.

(iv) Estimation of Radioactive Dose Remaining in Evacuated Suppository

The evacuated suppository was separated from the faecal pellet and weighed. The sample was then homogenised with a known quantity of purified sand (sand to sample ratio, 2:1).

Four pieces of the sand/suppository mixture were placed in weighed vials. Distilled water (4 ml) was added to each vial and the contents were allowed to dissolve overnight. Unisolve 1 (10 ml) was added and the resulting translucent gel was mixed by vigorous shaking. The samples were assayed for radioactivity.

(v) Estimation of Moisture Content of Evacuated Suppository

Three portions of the sand/suppository mix were weighed and freeze-dried at −35° C. and 0.07 Torr pressure for 2 days. They were then re-weighed and the moisture content of the evacuated suppository was determined.

RESULTS

A Preparation of Suppositories

Selection of Polymer

The hydroxypropyl methyl cellulose used in the initial study I above, "Methofas" PM 1,500 (produced by ICI Ltd.) was no longer available. The equivalent celluloses supplied by British Celanese Limited (Celacol) and the Dow Chemical Company Limited (Methocel) are identified in Table 1 below. These polymers are supplied in a range of molecular weights and different degrees of chemical substitution. It is common practice to describe them according to their viscosity (as 2% aqueous solutions at 20° C.).

The premium grades of these products are permitted as emulsifiers and stabilisers in the Ministry of Food regulations 1962 (Methocel Handbook, 1970. The Dow Chemical Company.; Cellanese Colloids, Technical Manual, British Cellanese Ltd.; and Methofas P. Technical Bulletin No. M1, I.C.I. Ltd. Nobel Division). Since the Methofas range is reported to have a high resistance to attack by microorganisms and also to be suitable for extrusion and moulding, Methocel E50 Premium (similar to Mechocel HG50) was chosen for further study.

Methods of Preparation (i) Compression moulding

Polymer mixes compressed in a mould at low pressures were unsatisfactory since the polymer particles did not bind together sufficiently.

(ii) Extrusion

It was found that certain ratios of polymer and water could be mixed to give a moist dough. These mixes were extruded at ambient temperature into a semi-rigid rod which could easily be cut into 3 cm lengths. The test products were made from mixtures containing polymer and water in a 1:1 ratio. They were sufficiently flexible not to break on bending and had a smooth surface finish. Although the extrusion pressure is probably less than that in compression moulding, the increased shear leads to improvised binding properties. Suppositories prepared in this way were used in the in vitro and in vivo trials.

B. In Vitro Trials

Drug release rates were measured in the in vitro trials for suppositories containing each drug alone and both drugs together. The total amount of drug in a suppository was calculated from the weight of the suppository and the quantity of drug in the original polymer mix. Correction was made for analytical background effects due to the polymer and the proportion of drug released at a given time was expressed as a percentage of the total.

It was found in suppositories containing each drug alone that the proportion of drug released was approximately the same for both phenylephrine hydrochloride and lignocaine hydrochloride (see FIGS. 6 and 7 of the accompanying drawings). Suppositories containing both drugs released approximately the same proportion of total drug in the same time (see FIG. 8 of the accompanying drawings).

In the same manner as just described for preparation of the suppositories employing hydroxypropylmethyl cellulose as the linear polymer, and employing the same ratios of materials and of therapeutically active ingredient, as well, of course, as the same amount of water, the following suppositories are prepared:

Polyvinyl Alcohol Suppositories

A number of grades of polyvinyl alcohol are available and these are generally classified according to the molecular weight and degree of hydrolysis. Typical average molecular weight ranges and characterizations, are as follows:

1. Super high viscosity 250,000–300,000
2. High viscosity 170,000–220,000
3. Medium viscosity 120,000–150,000
4. Low viscosity 30,000–35,000

An increase in the molecular weight is generally accompanied by a decrease in the ease of water solubility or water sensitivity, but not necessarily the extent of water solubility. Further, increases in molecular weight generally indicate an increase in tensile strength, tear strength, elongation, and flexibility of both thin and thick films. The degree of hydrolysis of the available polyvinyl alcohols include completely hydrolyzed grades, indicating 99 to 100% hydrolysis, and partially hydrolyzed grades, indicating 87 to 89% hydrolysis. Suppositories are formed in the manner described for hydroxypropylmethyl cellulose, as indicated, employing the super high viscosity and high viscosity grades of polyvinyl alcohol at both levels of hydrolysis. Extrudability of these suppositories is improved by inclusion of less than 1% glycerol as a plasticiser.

The results obtained with the polyvinyl alcohol suppositories are equivalent to those obtained with the hydroxypropylmethyl cellulose suppositories.

Polyvinyl Pyrrolidones

The polyvinyl pyrrolidones employable in formation of the suppositories of the present invention include both the homo-polymer of N-vinyl pyrrolidone, as well as blends of such polyvinyl pyrrolidone with up to 15% of a water soluble or water insoluble polymer, or one plasticised with a hydrophilic or hydrophobic compound. Among the water soluble polymers with which polyvinyl pyrrolidone is compatible are methyl cellulose and polyvinyl alcohol, while ethyl cellulose, cellulose acetate, and polyvinyl butyral are included in the water insoluble polymers. Hydrophilic plasticisers for polyvinyl pyrrolidone include diethylene glycol and sorbitol, while dimethyl phthalate is a hydrophobic plasticiser for polyvinyl pyrrolidone.

Polyvinyl pyrrolidone is available, commercially, with average molecular weights of 10,000, 40,000, 160,000 and 360,000.

Employing the same procedures as previously described for hydroxypropylmethyl cellulose suppository formation, and again with the same conditions, other materials, and ratios of materials, suppositories are prepared employing polyvinyl pyrrolidone with average molecular weights of 160,000 and 360,000, both alone and blended with 15% polyvinyl alcohol, where the polyvinyl alcohol has the same average molecular weight as the polyvinyl pyrrolidone with which it is blended.

Again, the results obtained with the polyvinyl pyrrolidone suppositories are equivalent to those obtained with the hydroxypropylmethyl cellulose suppositories.

Polyacrylamide Suppositories

Polyacrylamides are available with average molecular weights of from 30,000 to 11,000,000. Because of differences in film forming properties of the polyacrylamides as compared with the other linear polymers useful in accordance with the present invention, plasticisers, such as polypropyleneglycol and sorbitan monooleate-ethylene oxide adducts are employed in amounts of from 1 to 5% by weight of the polymer when forming the suppositories of the present invention.

Suppositories employing polyacrylamides, plasticised with 5% polypropyleneglycol in one case and sorbitan monooleate-ethylene oxide adducts in another, are prepared in the same manner as the hydroxypropylmethyl cellulose suppositories, with the same ratios of materials and same therapeutic compounds. The polyacrylamides employed in the formation of these suppositories have average molecular weights in the range of 100,000 to 400,000.

The results obtained are equivalent to those obtained from the suppositories formed with the hydroxypropylmethyl cellulose.

Modified Starches

The modified starches employable according to the present invention for forming suppositories are natural starches which have been chemically modified to improve many of the properties including gelling, adhesion, and film forming behavior. Among the modified starches employable according to the present invention are hydroxyethyl corn starches, having a degree of substitution of from 0.05 to 0.1 hydroxyl group per anhydroglucose unit, and hydroxypropyl starch ethers having essentially the same degree of substitution.

Suppositories are prepared in accordance with the present invention, employing the method, ratios, and other materials as previously described for formation of hydroxypropylmethylcellulose suppositories, in this case employing hydroxyethyl corn starch with a degree of substitution of 0.08 hydroxyl group (hydroglucose unit). The results obtained are equivalent to those obtained with suppositories formed from hydroxypropylmethylcellulose.

Figure 1:
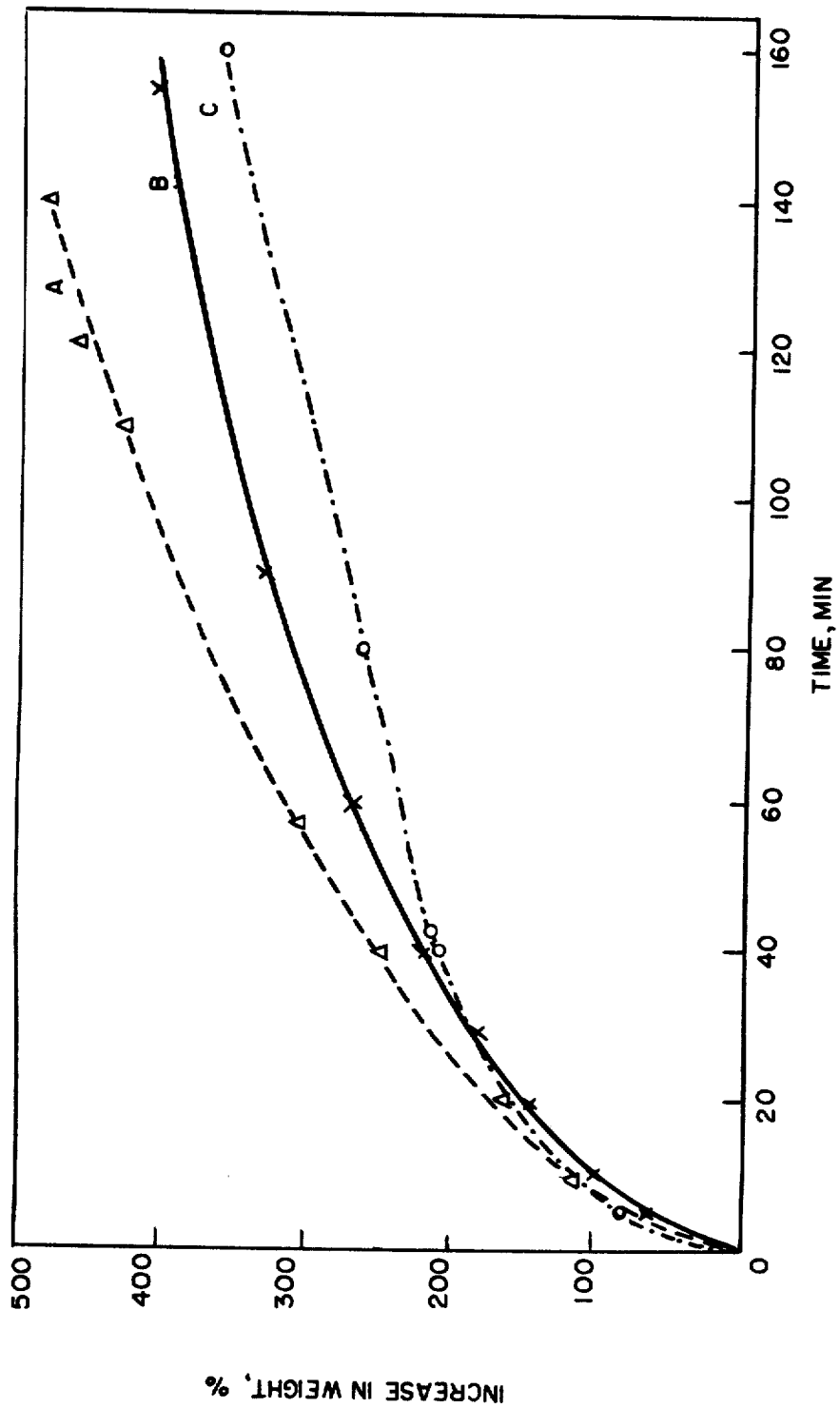
Figure 2:
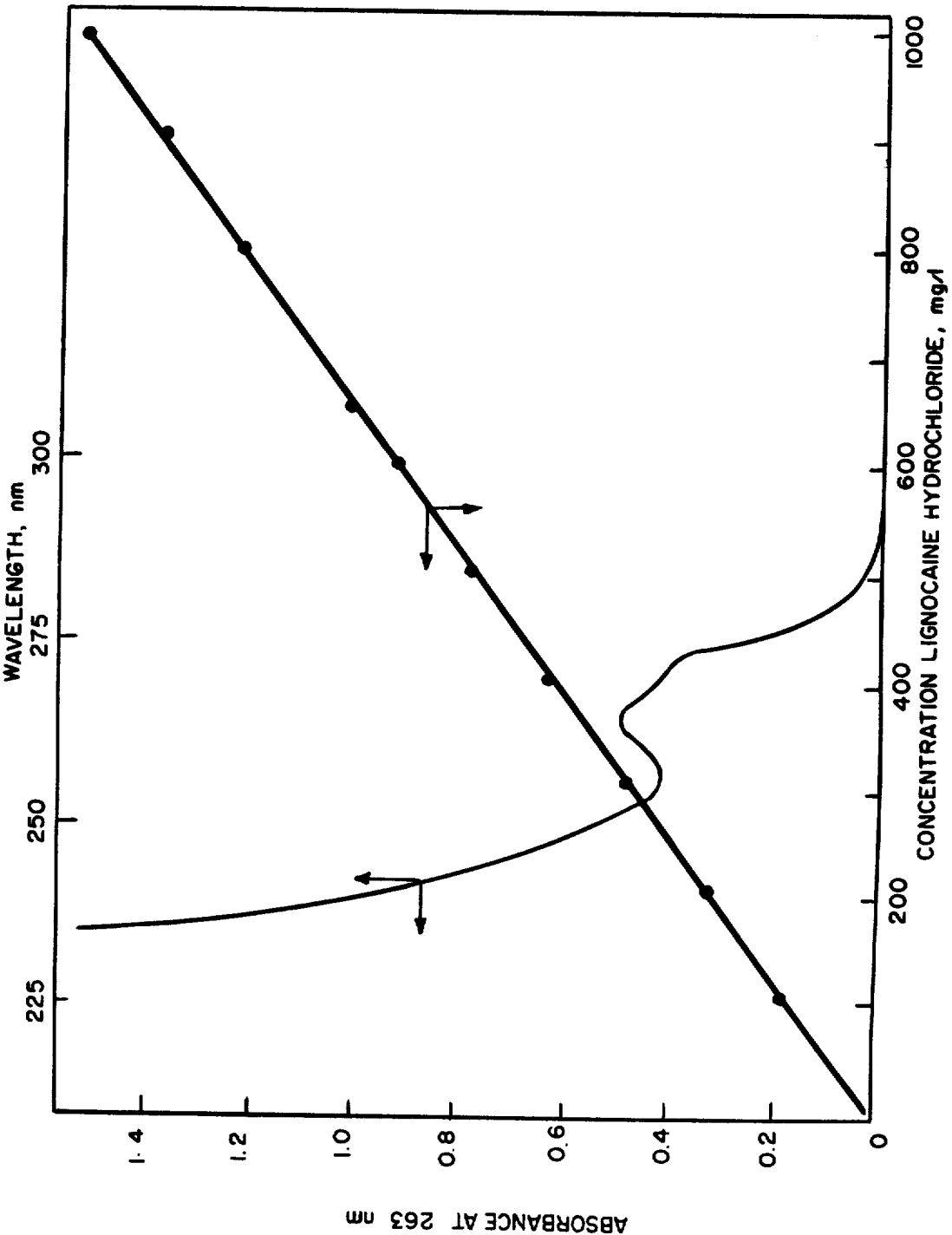
Figure 3:
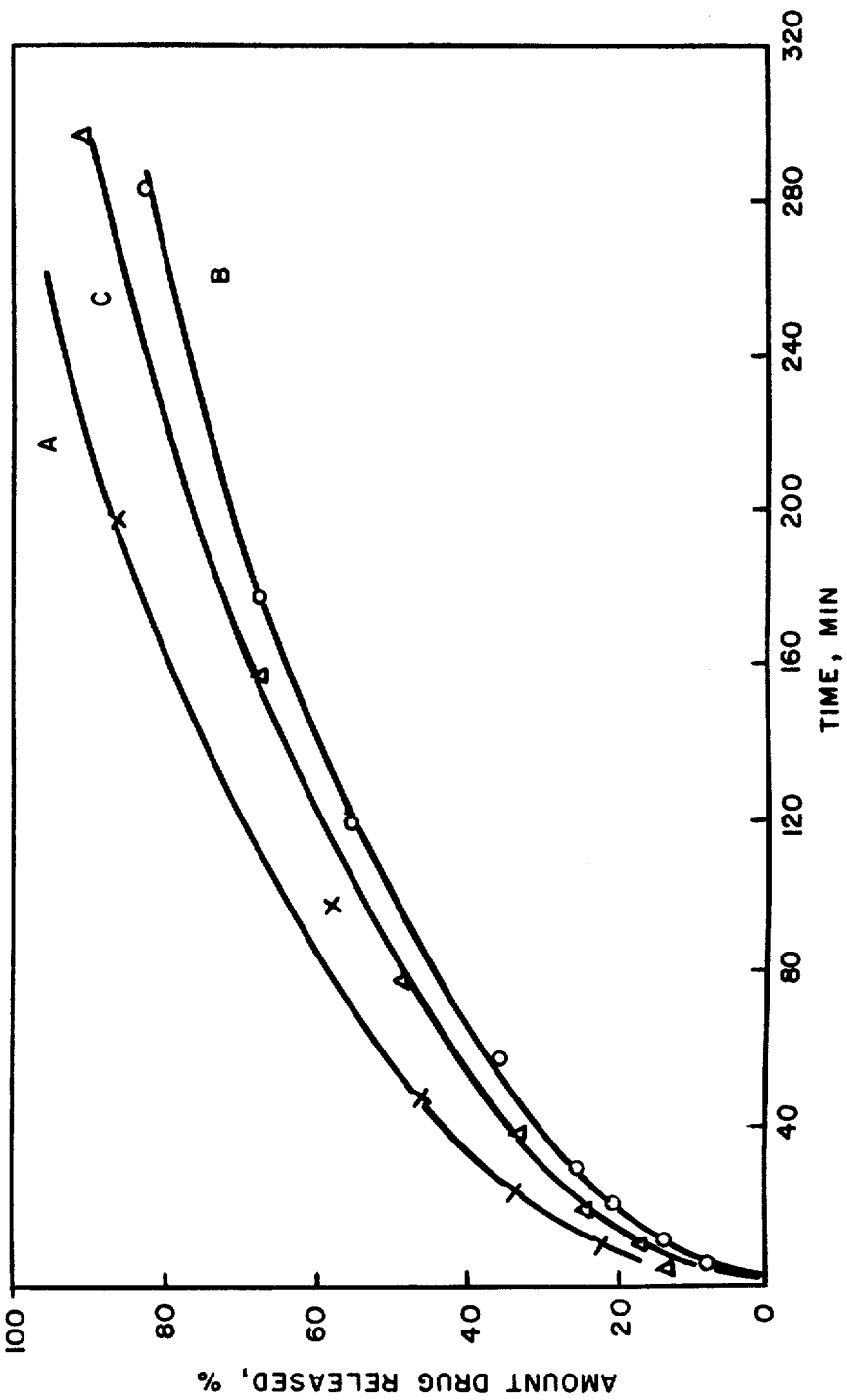
Figure 4:
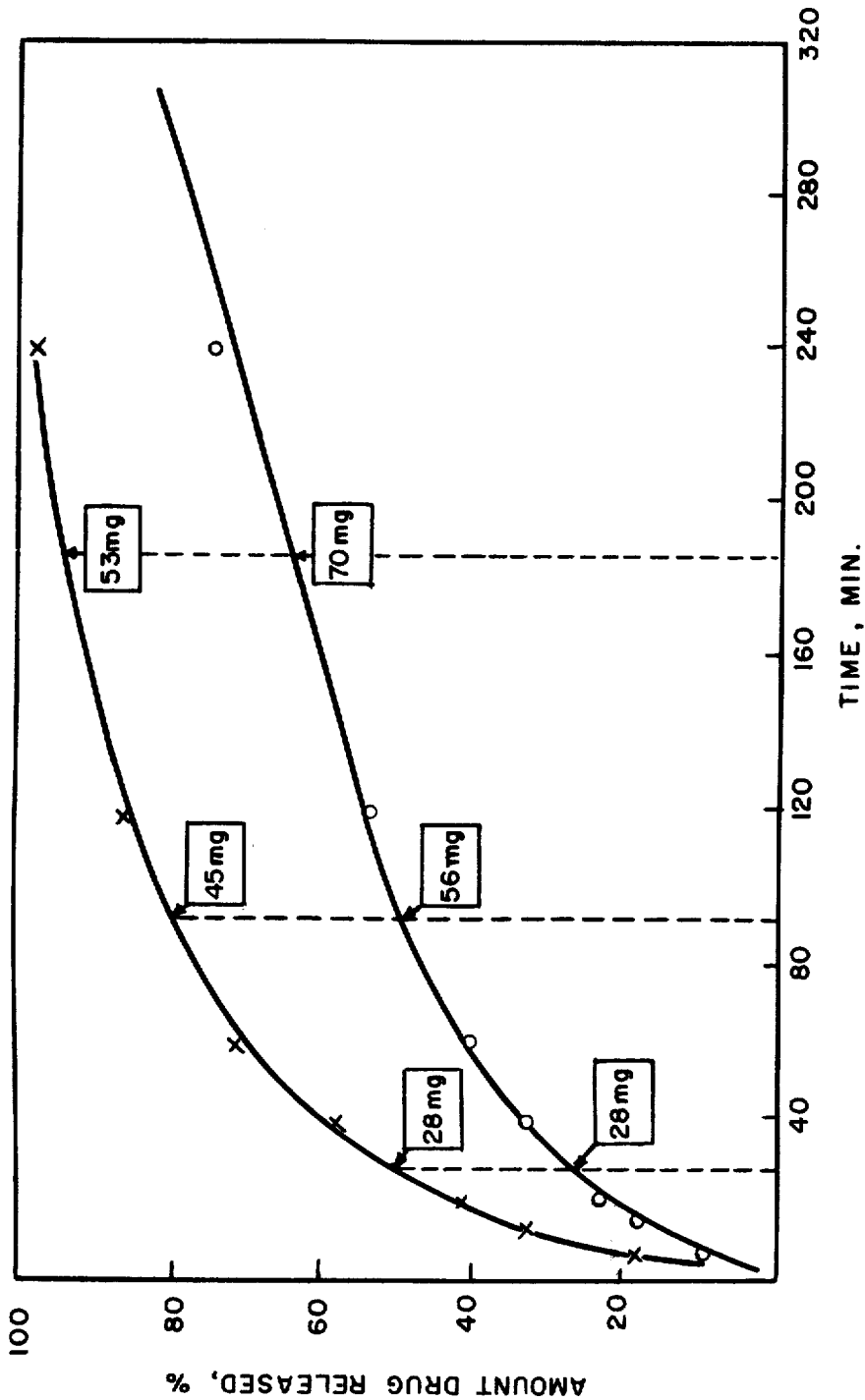
Figure 5:
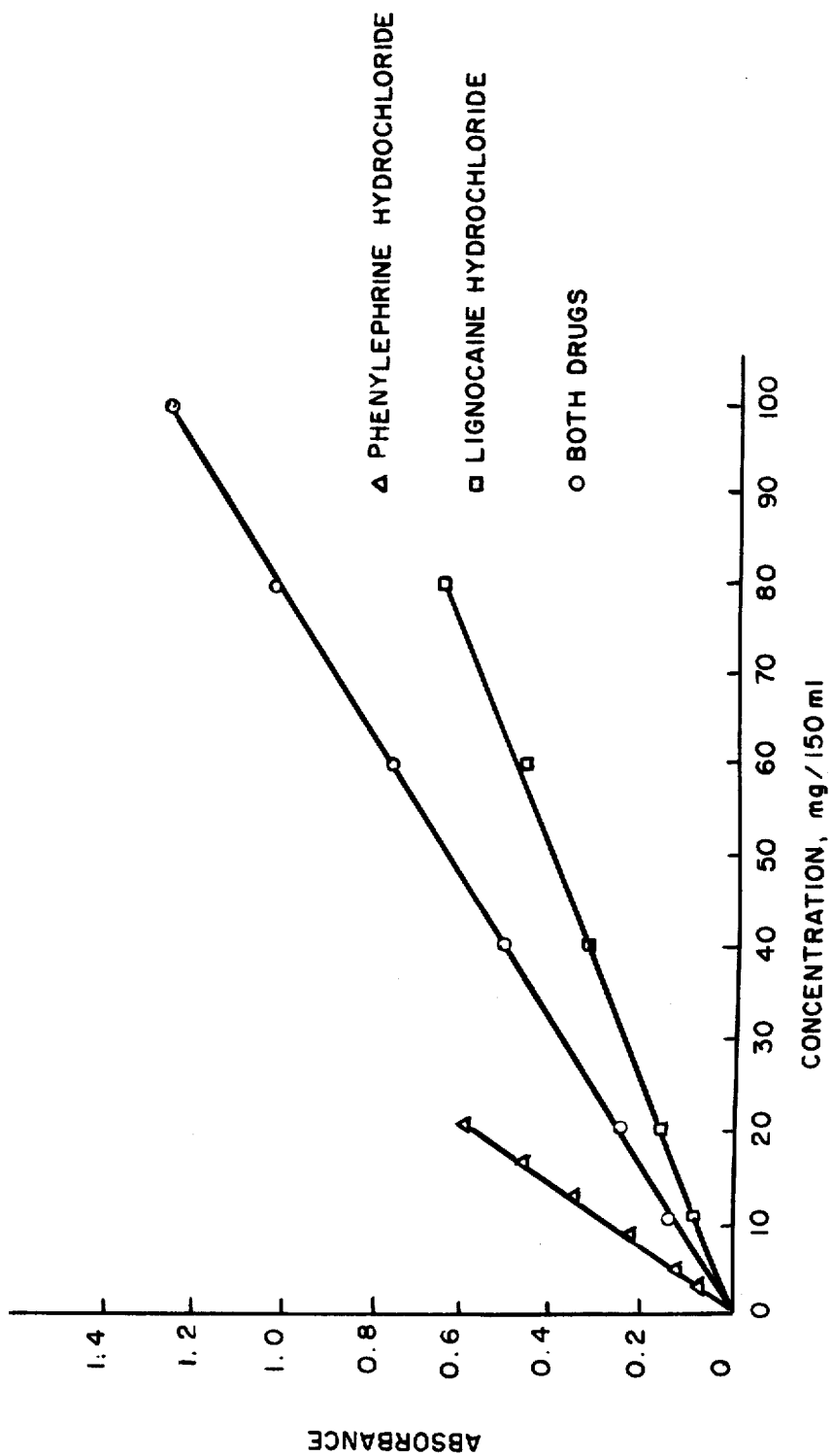
Figure 6:
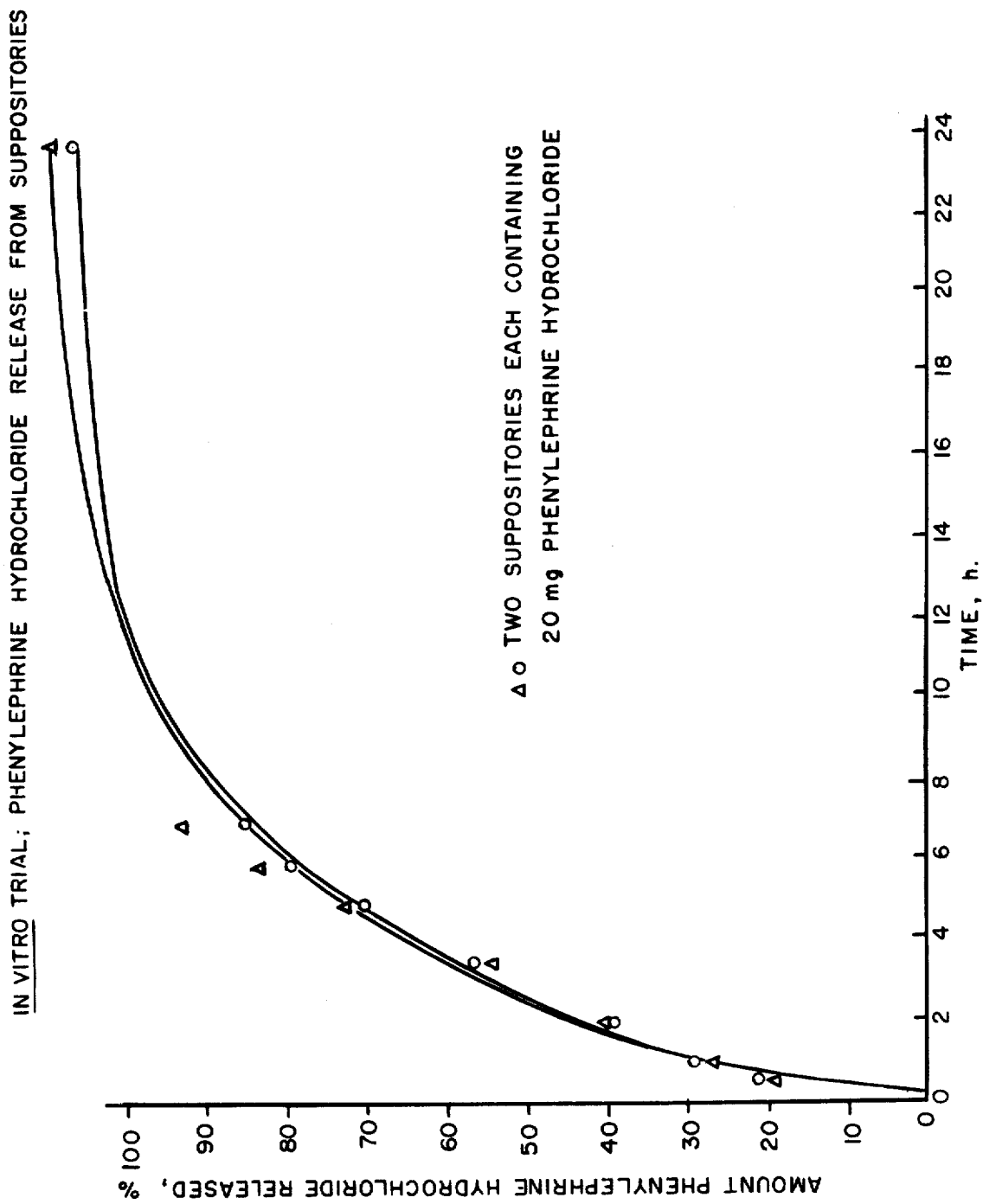
FIG. 6 is a graph of an in vitro trial of the release of phenylephrine hydrochloride from suppositories.
Figure 7:
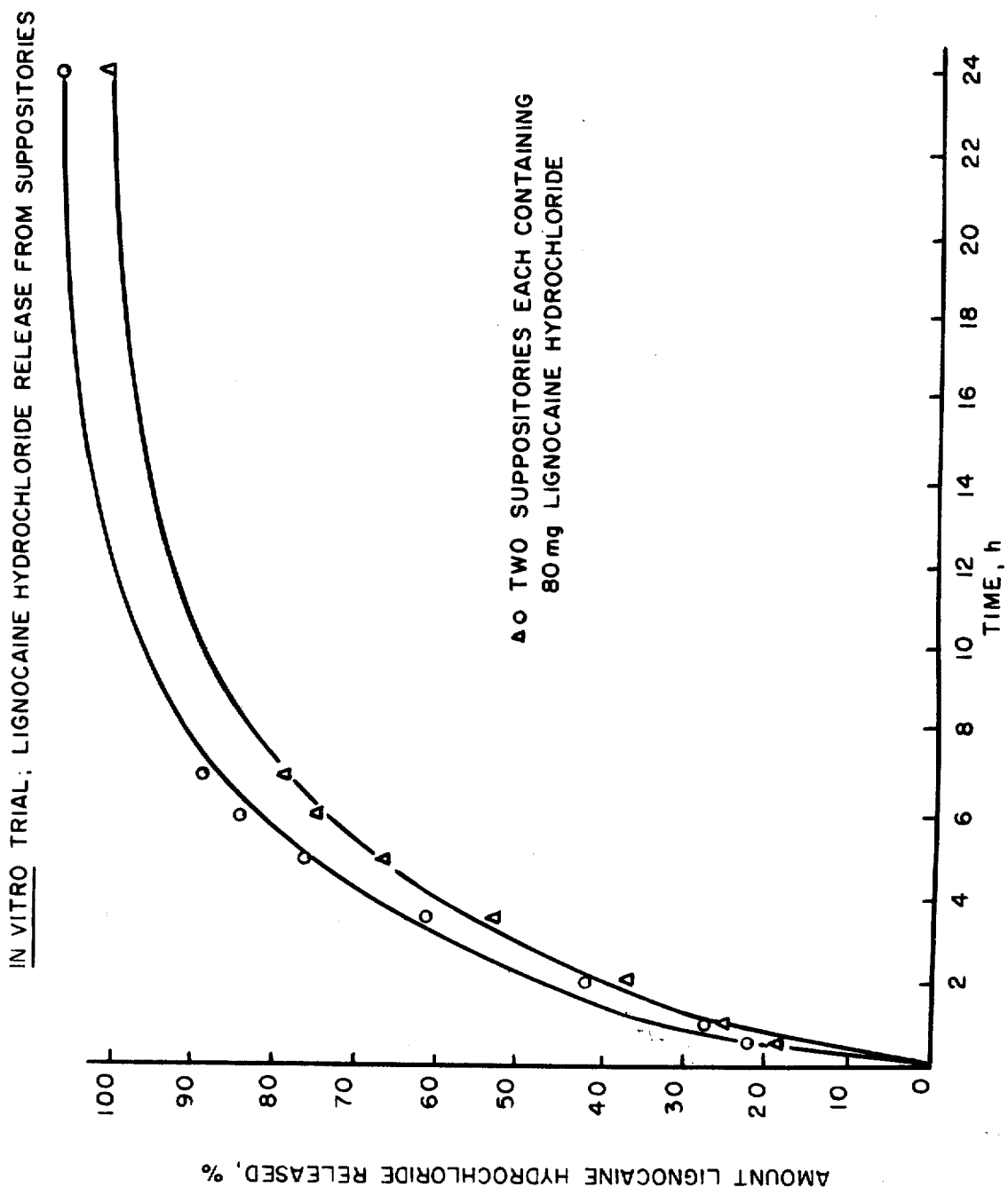
FIG. 7 is a similar graph relating to lignocaine hydrochloride.
Figure 8:
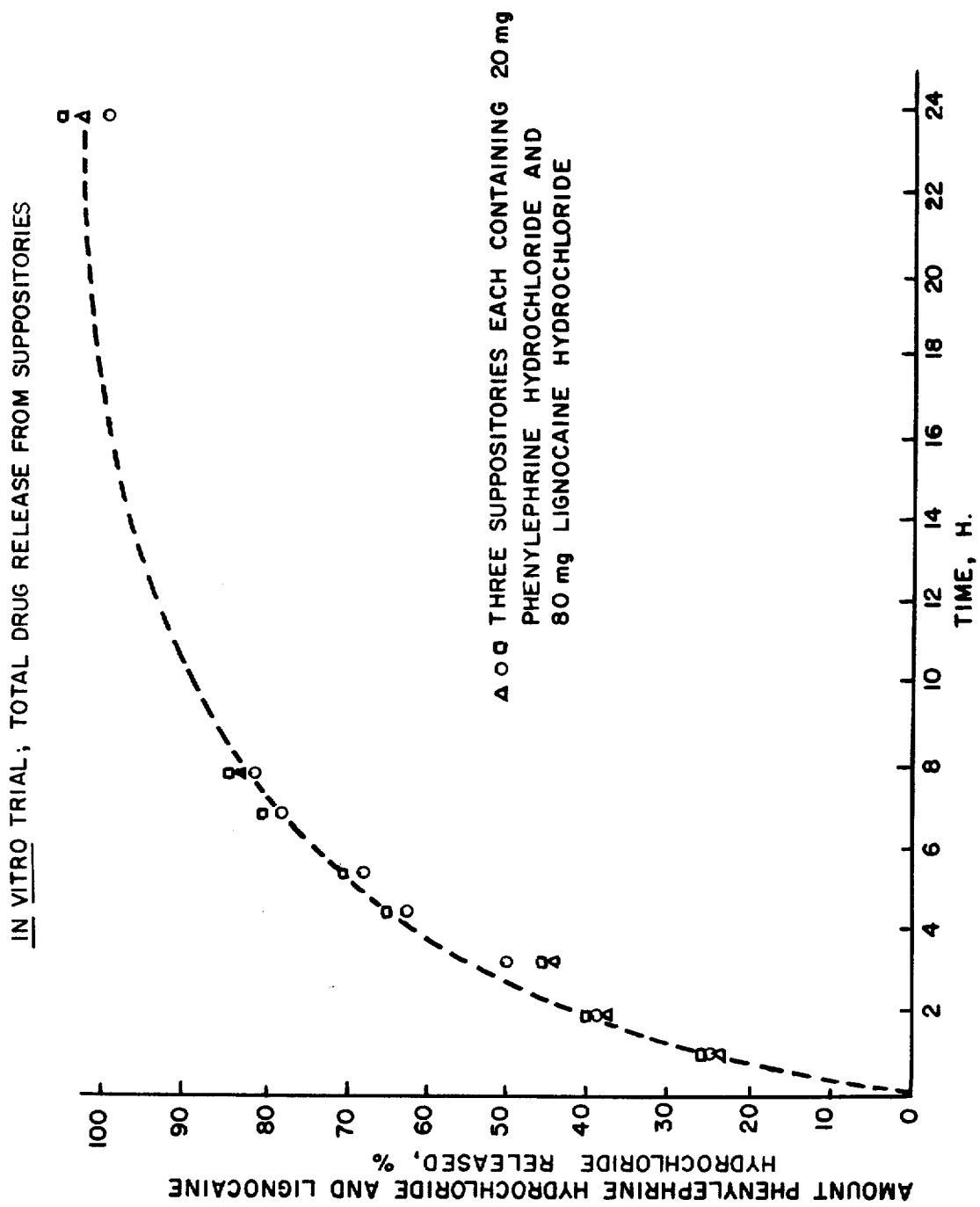
FIG. 8 is a graph of an in vitro trial of total drug release from suppositories.
Figure 9:
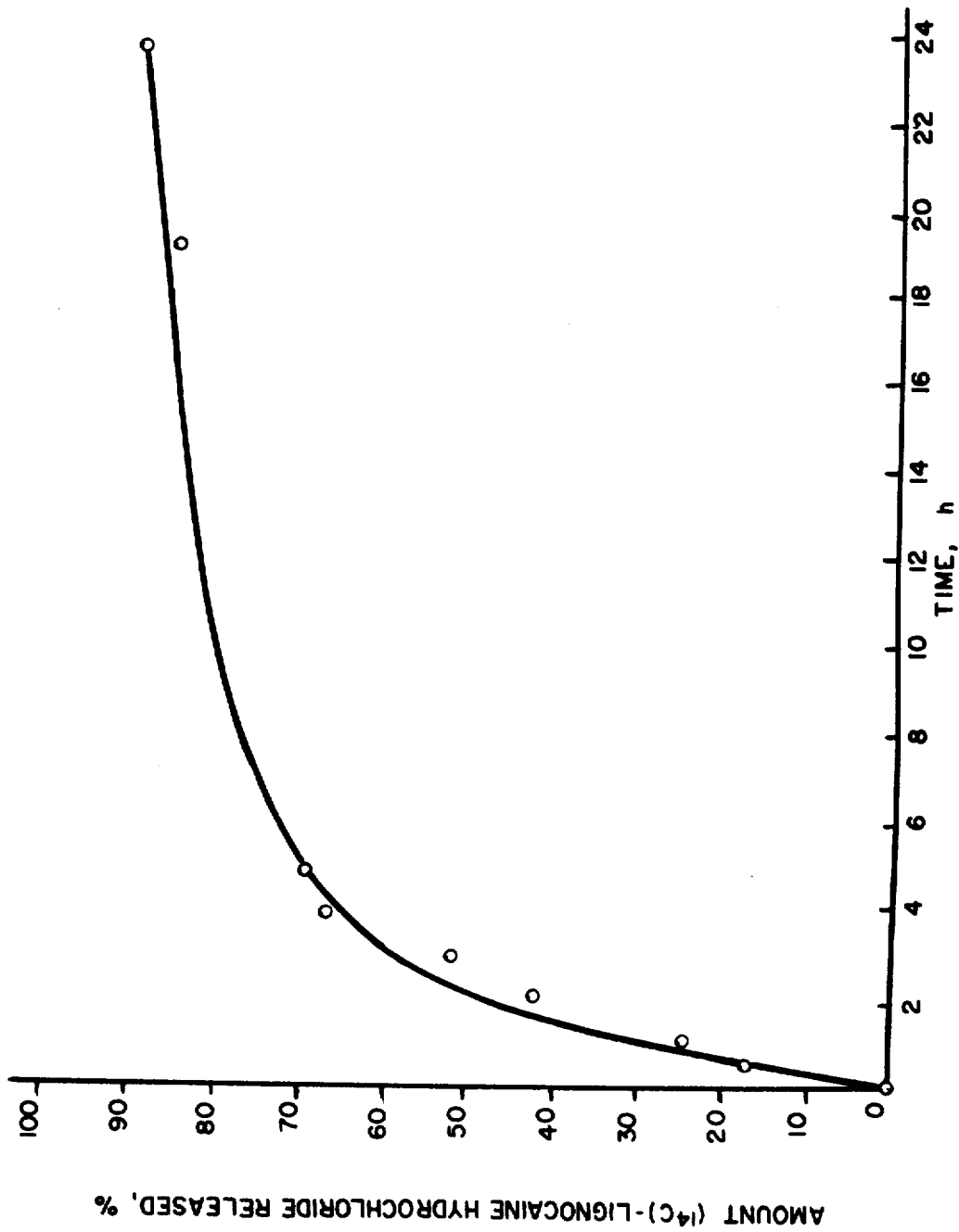
FIG. 9 is a graph of [$^{14}$C]-lignocaine hydrochloride in vitro release from suppositories.

The experiment in which the release rates of [$^{14}$C]-lignocaine hydrochloride was determined by assay for total radioactivity (FIG. 9) confirmed the results obtained spectrophotometrically.

In brief, about 50% of the total drug was released after 3 h, 80% after 8 h, and virtually all after 24 h.

C. In Vivo Trial (i) Radioactive Dose Administered

The radioactive dose administered in the suppository was 38.93 μCi.

(ii) Radioactive Dose Remaining in Evacuated Suppository

The radioactive dose remaining in the evacuated suppository was 10.74 μCi. Hence, 72.4% of the original radioactive dose had dispersed from the suppository.

(iii) Moisture Content of Evacuated Suppository

The moisture contents of the three portions of the evacuated suppository tested were 48.0%, 48.4% and 48.9%. This compares with a calculated moisture content of 47.6% in the suppository as prepared.

(iv) Plasma Total Radioactivity

Figure 10:
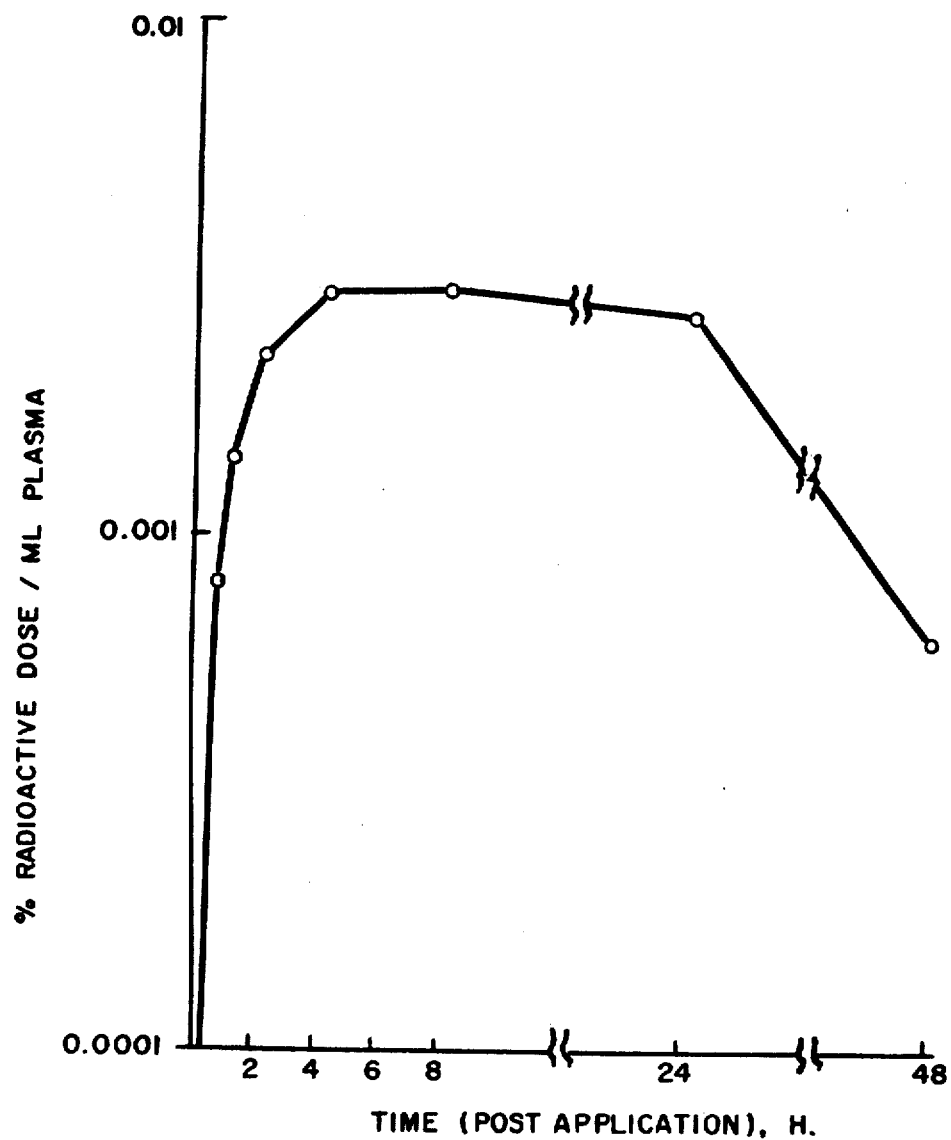

After the rectal administration of the [$^{14}$C]-lignocaine hydrochloride containing suppository, rapid absorption was noted; a plasma level of 0.0014%/ml of the administered radioactive dose being reached in the first hour. The maximum plasma concentration of radioactivity was reached at 8 h and was 0.00295%/ml of the administered radioactive dose, corresponding to 2.75 μgm/ml of [$^{14}$C]-lignocaine hydrochloride equivalents. A relatively steady plasma concentration of radioactivity was approached after 4 h and was maintained for a further 20 h (Table 2 and FIG. 10). FIG. 10 shows the concentration of radioactivity in dog plasma following administration of a suppository containing [$^{14}$C]-lignocaine hydrochloride.

The suppository was evacuated between the 10th and 24th hour after application. Without knowing the precise time of evacuation, it is not possible to determine a plasma half life. It is clear, however, that the drug is quite rapidly removed from the blood stream.

(v) Total Radioactivity in Excreta 40.16% of the total administered radioactive dose was excreted in the urine over the 48th collection period; 34.54% of this was recovered in the first 24 h. 8.04% of the original dose was excreted in the total faecal sample. 48.2% of the administered radioactive dose therefore, was excreted over 48 h (Table 3).

(vi) Total Radioactivity in Tissues

Levels of radioactivity in bile, liver, rectum and rectal contents were 0.015, 0.36, 0.026 and 0.086% of the total administered radioactive dose respectively (Table 4).

TABLE 1

| Viscosity[1] range (cps) | Hydroxypropyl methyl celluloses (identified in terms of viscosity type) (Refs. 1, 2 and 4) | | |
|---|---|---|---|
| | Celacol[2] | Methocel[3] | Methofas[4] |
| 10 | | 60HG(50) | PM50 |
| | | 65HG(50) | |
| 100 | | 90HG(100) | |
| | | | PM125 |
| | | 90HG(400) | |
| | HPM450 | | PM450 |
| 1000 | | | |
| | | | PM1500 |
| | | 60HG(4000) | |
| | | 65HG(4000) | PM4500 |
| | HPM5000 | 90HG(4000) | |
| | | | PM6000 |
| | HPM15000 | 90HG(15000) | PM15000 |
| | | | PM15000 |
| | HPM30000 | | |
| 100000 | | 90HG(50000) | |

[1]In 2% aqueous solution at 20° C.
[2]Celacol range from British Celanese Limited.
[3]Methocel range from The Dow Chemical Company Limited, (bracketed figures denote viscosity).
[4]Methofas range from I.C.I. Limited. This range is no longer commercially available.

TABLE 2

Concentrations of radioactivity and radioactive drug equivalents in the plasma of a male beagle following rectal administration of a suppository containing [$^{14}$C]—lignocaine hydrochloride.
Radioactive dose: 38.93 μCi.

| | Concentrations/ml plasma | |
|---|---|---|
| Time, h | % administered radioactive dose | μg equivalents |
| 0 | 0 | 0 |
| 0.5 | 0.00081 | 0.75 |
| 1 | 0.0014 | 1.33 |
| 2 | 0.0022 | 2.08 |
| 4 | 0.00291 | 2.72 |
| 8 | 0.00295 | 2.75 |
| 24 | 0.00267 | 2.49 |
| 48 | 0.00062 | 0.58 |

TABLE 3

Total radioactivity excreted by a male beagle following rectal administration of a suppository containing [$^{14}$C]—lignocaine hydrochloride.
Radioactive dose: 38.93 µCi.

| Sample | Total Radioactivity (µCi) | % Total administered dose |
|---|---|---|
| 0–24 h urine | 13.45 | 34.54 |
| 24–48 h urine | 2.19 | 5.62 |
| Total faeces | 3.13 | 8.04 |
| Total excreted | 18.77 | 48.20 |

TABLE 4

Total radioactivity recovered in the tissues and excreta of a male beagle following rectal administration of a suppository containing [$^{14}$C]—lignocaine hydrochloride.
Radioactive dose: 38.93 µCi.

| Sample | Total Radio-activity (µCi) | % Total Administered Dose | Cumulative % Total Administered Dose |
|---|---|---|---|
| Bile | 0.006 | 0.015 | 0.015 |
| Liver | 0.14 | 0.36 | 0.375 |
| Rectum | 0.01 | 0.026 | 0.401 |
| Rectal contents | 0.03 | 0.086 | 0.487 |
| Urine and faeces | 18.77 | 48.20 | 48.687 |
| Evacuated Suppository | 10.74 | 27.58 | 76.27 |

A. Preparation of Suppositories

A critical step in the preparation of the suppositories is mixing. It is essential that a homogeneous mix be obtained, otherwise reproducible drug release rates could not be guaranteed. Manual mixing was satisfactory for laboratory study but mechanical mixing is needed on a process scale.

Limited attempts to make the suppositories by compression moulding were unsuccessful; mechanically weak products were formed and localised thermal degradation sometimes occurred if high temperatures were employed.

Extrusion at room temperature proved to be a simpler, yet effective technique; the products possessed good mechanical strength and satisfactory elasticity. Since heat is not required, thermal degradation and volatilisation of water did not occur.

B. In Vitro Trials

The in vitro trials have rapid feedback on the reproducability of drug release rate, and, indirectly of mixing. However, it should be appreciated that these experiments do not necessarily imitate the in vivo situation since, in these tests, the drugs are released directly into a large volume of water.

Excellent reproducibility of drug release rates was found.

C. In Vivo Trial

The release properties of the suppository in vivo were comparable with those observed in the in vitro trials. Thus, the 80% during liberation at 8 h in vitro is quite compatible with the observed 72% up to evacuation in vivo between the 10th and 24th hour after administration. The lignocaine released is predictably well absorbed with only 8% of the dose being recovered in faeces at 48 h. The plasma concentration and time curve shows the characteristics expected from a sustained release formulation. While we have no means of determining the anaesthetic concentration at the rectal mucosa, it is reasonable to infer that the plasma concentrations also reflect sustained levels at the intended site of action.

It was interesting to note, that, after evacuation the shape and water content of the suppositiory were essentially unchanged from those of the original.

The fact that the water content of the suppository dose did not change in vivo suggested that suppositories with higher water to polymer ratios could be made (using higher molecular weight cellulose ethers).

As regards the potential of the rectal route for lignocaine as an alternative to intravenous infusion in certain areas of cardiology, enhanced systemic bioavailability when compared with the oral route could be anticipated. A large proportion, approximately 65% of an oral dose of lignocaine is metabolised in passing through the liver in the portal circulation. The considerable quantities of metabolites which are formed rapidly may account for some of the problems encountered in oral lignocaine therapy (see e.g. Boyes, R. N. and Keenaghan, J. B. in Scott, D. B., and Julian D. G. (editors), "Lidocaine in the treatment of ventricular arrhythmias" pages 140-151, Livingston (1971); and Boyes, R. N. Scott, D. B. Jebson, P. J. Godman, M. J. and Julian D. G., Clin. Pharm. Therap., 12, 105–116 (1971). Avoidance to some extent of "first pass" hepatic metabolism is achieved when a drug is given rectally since both the systemic and portal circulations are supplied through the haemorrhoidal plexus. The promotion of rectal lignocaine in the treatment of, for example, venticular arrhythmias would however require the demonstration that this vehicle led to the sustained blood levels of free drug in the manner currently achieved only by slow intravenous infusion.

Attempts to Make Suppositories Containing 30% and 35% Water

We have attempted to make suppositories containing 30% and 35% water by the discussed extrusion process. In no case has a satisfactory mechanically stable suppository been formed.

Our method involves mixing the polymer with liquid water (containing the drug) until a homogeneous 'dough' is produced. The 'dough' is then extruded to yield a rod which can be cut into individual suppositories. In all cases with a '30% or 35% by water product' the resultant suppositories consisted of a mass of granules lacking the necessary coherence; thus the product was unsuitable for in vivo experiments.

Attempts were made to make suppositories containing 30% and 35% water by a compression technique using a device which comprises a plunger having an end shaped to give a first rounded end to the suppository. The plunger is adapted to fit into a circular hole in a suppository mould main component. An end piece is adapted to screw onto the suppository mould main component, which end piece is provided with a shape well adapted to give a second rounded end to the suppository. The suppository mix is placed in the circular hole in the suppository mould main piece and compressed by the plunger. At low pressures (e.g. up to 30 lbs./sq. inch, the product lacked cohesion and mechanical stability; most were so fragile that they could easily be broken by slight finger pressure. At higher pressures (at least 100 lbs./sq. inch) the product was more mechanically stable but only as a result of a thin (1 mm) outer film which encases polymer granules lacking in cohesion. These products were also unsuitable for in vivo experiments.

FURTHER DETAILED IN VIVO STUDIES INCLUDING COMPARISON OF SUPPOSITORIES OF PRESENT INVENTION WITH COMMERCIALLY AVAILABLE SUPPOSITORIES

Method

Experiment A

A single batch of suppositories containing $^{14}$C-labelled lignocaine was prepared according to the following formulation and method. The formulation of each 2 g suppository was as follows:

Polymer: 1 g
Water 1 g
Lignocaine HCl (labelled and unlabelled drug): 40 mg
Phenylephrine HCl: 2 mg
Betamethasone disodium phosphate: 0.54 mg An amount of mix was prepared sufficient for the manufacture of twenty 2 g suppositories. From the extruded rod suppositories of 3 cm length were cut. Each suppository was weighed, wrapped in aluminium foil and stored at 4° C. until use.

After every second suppository, a small section weighing approximately 0.1 g was removed and used to determine the distribution of radioactivity along the rod. The sample was dissolved in 100 ml distilled water, from which aliquots were removed and counted for total radioactivity. The average radioactivity in 9 samples was 0.0136 μCi/mg and gave a standard deviation of (6%) of ±5.2%.

A comparison of these suppositories with the commercially available low melting wax suppositories, "Betnovate" (Glaxo), contaning the same quantity of lignocaine hydrochloride as the suppository of the present invention was made. For this comparison, lignocaine in plasma was determined specifically using a gas chromatographic method (K. K. Adjepon-Yamoah and L. F. Prescott, *J. Pharm. Pharmac.*, 26, 889–893 (1974)). A Perkin-Elmer F 17 gas chromatograph equipped with a nitrogen-selective detector was used. The detection limit was approximately 5 ng/ml.

Figure 11:
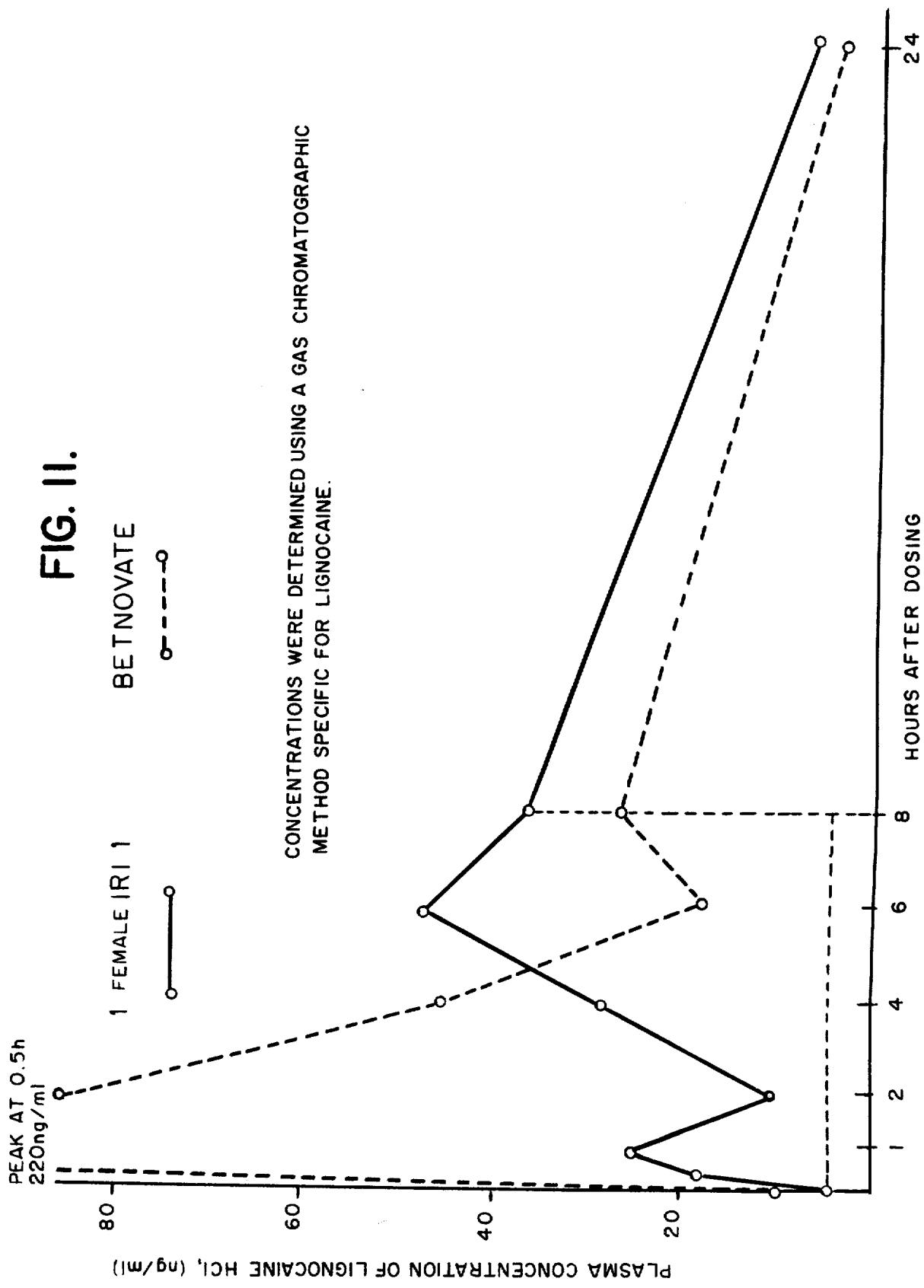

This wax suppositories resulted in a relatively rapid release and decline of plasma lignocaine (for example FIG. 11), and evidence was obtained for a slow release of lignocaine from the suppository of the present invention.

Experiment B (with a larger group of 6 animals)

A fresh batch of 20 suppositories containing 14C-lignocaine was prepared as above. Six were used "fresh" i.e. within 24 hours and six 14 days later ("aged") using the same group of dogs. Radioactivity was determined in plasma and in the evacuated suppositories by the following method (a) Body Fluids Aliquots of plasma and urine (in triplicate) were added directly to scintillator for determination of radioactivity by liquid scintillation counting.

(b) Evacuated suppositories

Evacuated suppositories were separated as far as possible from attached faeces and added to a pre-weighed quantity of purified sand, re-weighed (approximately sand:sample ratio 2:1) and then homogenised using a mortar and pestle. Approximately 0.05 g quantities of the sand: suppository mixture were weighed in triplicate, dissolved in water overnight and counted for total radioactivity.

Figure 12:
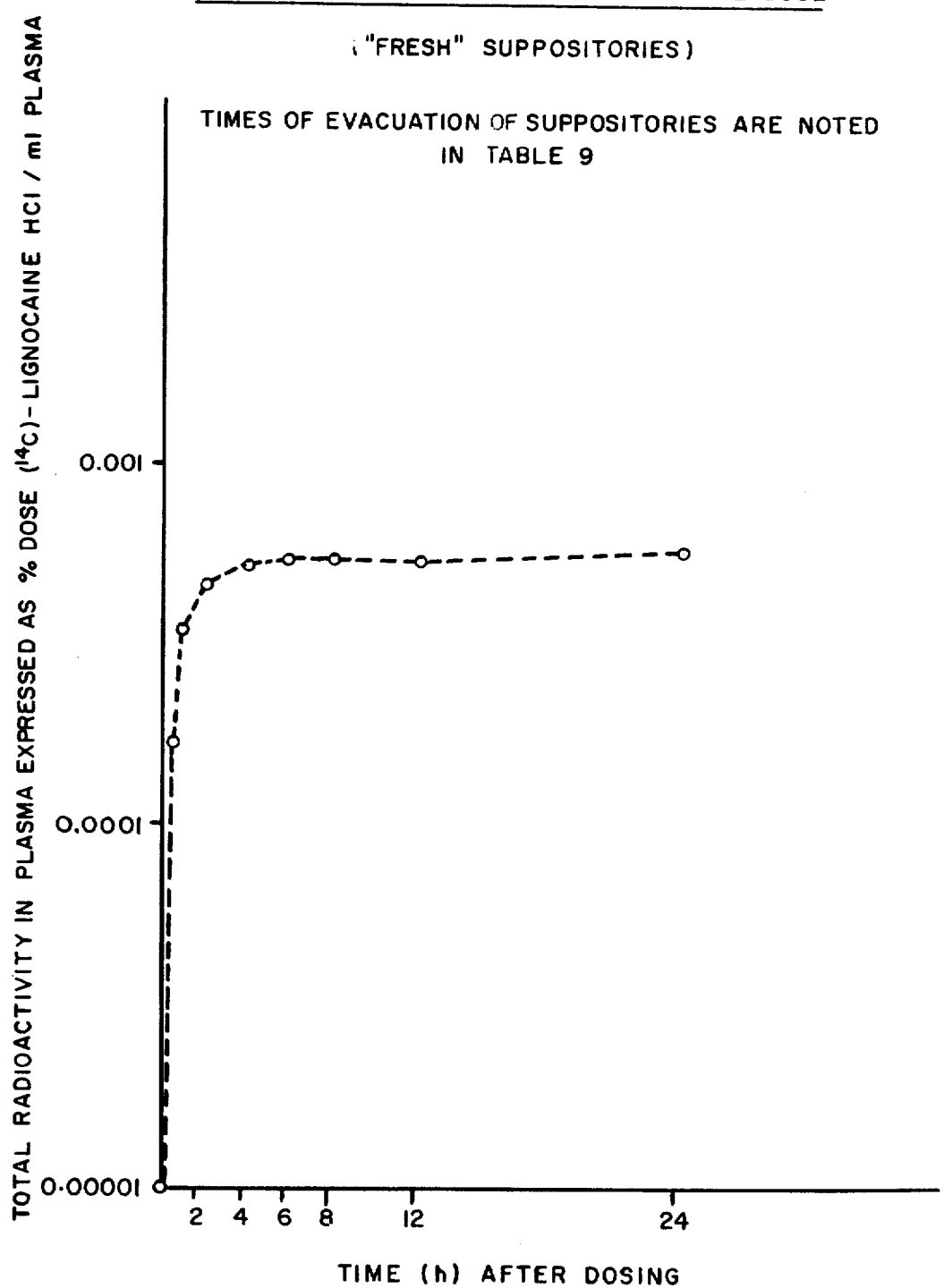
Figure 13:
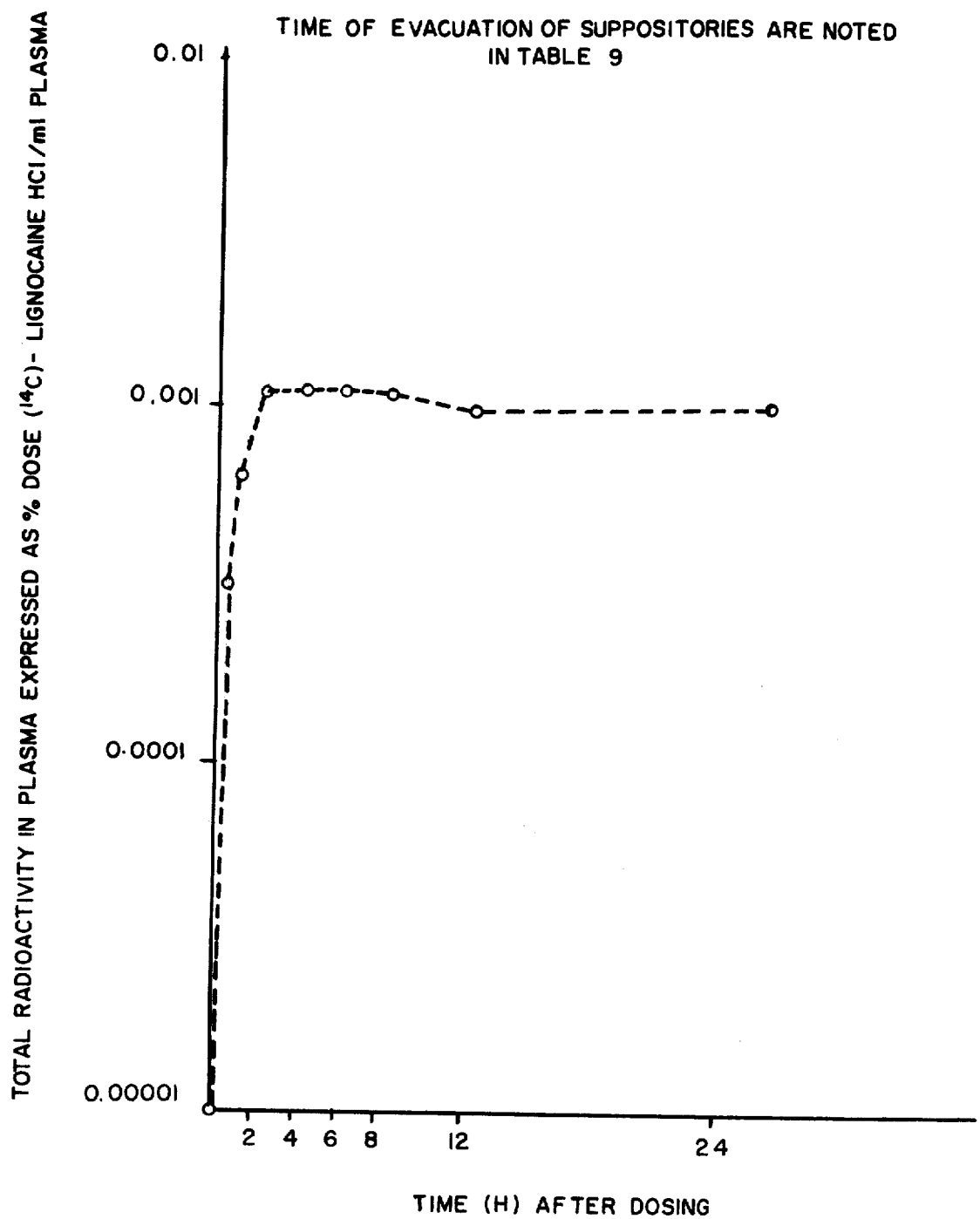

The mean plasma concentration time profiles for the "fresh" group and the "aged" group are shown in FIGS. 12 and 13 respectively. Dogs 1 male and 3 male have been excluded since in both cases, evacuation of suppositories occurred shortly after insertion ($\leq 1.0$ h). Values of concentration for individual animals are presented in Table 5 as nanogram equivalents of lignocaine/ml and in Table 6 as % dose/ml. Table 7 shows the times of suppository evacuation and the residual $^{14}$C contact of the suppositories.

While there is a marked inter-animal variation in the release characteristics and in one case (animal 3 male, fresh) a distinctly anomalous result, the data shown in FIGS. 12 and 13 strongly support the contention of sustained release behaviour. The 0–8 h AUC values are presented in Table 8 and generally where higher residual concentration have been recorded in the evacuated suppositories, these are associated with rather lower values of the AUC.

Summary of Results (i) Slow release of lignocaine (evaluated as total radioactivity appearing in peripheral plasma) from the suppository of the present invention is now substantiated. Examination of the figures demonstrates some variability between experiments (due to possible minor differences in the distribution of lignocaine in individual suppositories and/or to inter-animal variability). However, such variability is not unexpected in such studies.

(ii) Compared with Betnovate suppositories, the suppository of the present invention releases less lignocaine in the period 0–8 h. It is emphasised that the release behaviour of the Betnovate suppository is not considered to be of the slow release type and is characteristic of a suppository which melts rectally and relatively rapidly releases the drug.

It is important to remember that at the present time, the effective minimum local concentration of lignocaine is unknown and the release behaviour of the suppository of the present invention demonstrated in this experiment may be satisfactory for general purposes.

TABLE 5

[$^{14}$C]—Lignocaine HCl concentration in dog plasma
after suppository (IRI) administration
Total radioactivity was determined and results are expressed
as ng equivalents Lignocaine/ml

| Dog No. | Preparation | Plasma concentration of Lignocaine HCl (ng equiv/ml) | | | | | | | | |
|---|---|---|---|---|---|---|---|---|---|---|
| | | 0 h | 0.5 h | 1 h | 2 h | 4 h | 6 h | 8 h | 12 h | 24 h |
| 1 MALE | IRI (fresh) | 0 | 19 | 38 | 88 | 152 | 202 | 224 | 170 | 119 |
| 2 MALE | IRI (fresh) | 0 | 274 | 425 | 468 | 441 | 350 | 308 | 290 | 527 |
| 3 MALE | IRI (fresh) | 0 | 0 | 0 | 0 | 0 | 0 | 0 | 0 | 0 |
| 4 FEMALE | IRI (fresh) | 0 | 48 | 123 | 116 | 105 | 110 | 124 | 135 | 190 |

TABLE 5-continued

[$^{14}$C]—Lignocaine HCl concentration in dog plasma after suppository (IRI) administration
Total radioactivity was determined and results are expressed as ng equivalents Lignocaine/ml

| Dog No. | Preparation | \multicolumn{9}{c}{Plasma concentration of Lignocaine HCl (ng equiv/ml)} |
|---------|-------------|-----|-------|-----|-----|-----|-----|-----|------|------|
|         |             | 0 h | 0.5 h | 1 h | 2 h | 4 h | 6 h | 8 h | 12 h | 24 h |
| 5 FEMALE | IRI (fresh) | 0 | 108 | 237 | 338 | 315 | 253 | 252 | 228 | 150 |
| 6 FEMALE | IRI (fresh) | 0 | 0   | 38  | 137 | 297 | 449 | 453 | 511 | 429 |
| x̄ |             | 0 | 75  | 143 | 192 | 218 | 227 | 227 | 223 | 236 |
| 1 *MALE  | IRI (aged)  | 0 | 40  | —   | —   | —   | —   | —   | —   | —   |
| 2 MALE   | IRI (aged)  | 0 | 8   | 7   | 8   | 17  | 27  | 37  | 55  | 166 |
| 3 **MALE | IRI (aged)  | 0 | 0   | 8   | —   | —   | —   | —   | —   | —   |
| 4 FEMALE | IRI (aged)  | 0 | 172 | 335 | 485 | 530 | 537 | 525 | 467 | 487 |
| 5 FEMALE | IRI (aged)  | 0 | 227 | 389 | 577 | 607 | 571 | 548 | 537 | 479 |
| 6 FEMALE | IRI (aged)  | 40| 360 | 607 | 812 | 824 | 733 | 670 | 604 | 506 |
| x̄ |             | 7 | 134 | 269 | 470 | 494 | 465 | 453 | 416 | 410 |

*1 MALE defaecated after 0.75 h.
**3 MALE defaecated after 1.0 h
Other times of evacuation of suppositories are noted in Table 7.

TABLE 7

Times of suppository (IRI) evacuation and % dose recovered

| Dog No. | Preparation | Time of excretion post-dose | % $^{14}$C dose recovered in evacuated suppository |
|---------|-------------|------------------------------|------------------------------------------------------|
| 1 MALE   | IRI (fresh) | 12–24 h        | 35.4         |
| 2 MALE   | IRI (fresh) | not recovered  | —            |
| 3 MALE   | IRI (fresh) | 8–12 h         | 40.8         |
| 4 FEMALE | IRI (fresh) | 28 h           | 16.1         |
| 5 FEMALE | IRI (fresh) | 12–24 h        | (not intact) |
| 6 FEMALE | IRI (fresh) | 36–47 h        | 9.0          |
| 1 MALE   | IRI (aged)  | 45 mins        | 69.1         |
| 2 MALE   | IRI (aged)  | 12–24 h        | 42.1         |
| 3 MALE   | IRI (aged)  | 1 h 12 mins    | 74.8         |
| 4 FEMALE | IRI (aged)  | 32–48 h        | 10.3         |
| 5 FEMALE | IRI (aged)  | 12–24 h        | 23.6         |
| 6 FEMALE | IRI (aged)  | 12–24 h        | 12.5         |

TABLE 8

Areas under the plasma lignocaine*-time curves following administration of IRI (fresh) and IRI (aged) suppositories

| Dog No. | Preparation | AUC 0–8 h (ng ml$^{-1}$ h) |
|---------|-------------|-----------------------------|
| 1 MALE   | IRI (fresh) | 1095 |
| 2 MALE   | IRI (fresh) | 3008 |
| 3 MALE   | IRI (fresh) | 0 |
| 4 FEMALE | IRI (fresh) | 830 |
| 5 FEMALE | IRI (fresh) | 2123 |
| 6 FEMALE | IRI (fresh) | 2192 |
| Mean (excluding 1 male and 3 male) | | 2038 |
| 1 MALE   | IRI (aged)  | excreted after 0.75 h |
| 2 MALE   | IRI (aged)  | 145.0 |
| 3 MALE   | IRI (aged)  | excreted after 1.0 h |
| 4 FEMALE | IRI (aged)  | 3722.5 |
| 5 FEMALE | IRI (aged)  | 4168 |
| 6 FEMALE | IRI (aged)  | 5678.5 |
| Mean (excluding 1 male and 3 male) | | 3428.5 |

*Total radioactivity in plasma was determined and concentrations are based upon ng equivalents of lignocaine HCl/ml based on the specific activity of the dose.

The use of polymers has several advantages: Many polymers are stable to heat (up to at least 100° C.) and light, they do not change colour or emit odours on storage. They can be made in ionic or non-ionic form and with hydrophilic or hydrophobic properties. They are therefore compatible with a wide range of drugs. They do not melt to form messy fluids.

Because of this high molecular weight and insolubility (or low solubility) they are not absorbed by the body or have only a low absorption.

Another typical suppository drug composition (in addition to those already described) is 1. lignocaine hydrochloride (80 mg), phenyl ephrine hydrochloride (20 mg), and betamethasone sodium phosphate (0.54 mg)

Betamethasone is a steroid. Other water soluble steroids which may be used include prednisolone metasulphobenzoate (sodium salt), prednisolone phosphate (disodium salt), methyl prednisolone sodium succinate, dexamethasone sodium phosphate, hydrocortisone sodium phosphate.

We claim:

1. A non-dissolving, non-disintegrating slow-release shaped suppository consisting essentially of polyvinyl pyrrolidone, water, and a therapeutically effective amount of a water-soluble therapeutically active ingredient, wherein the water is present in an amount of more than 35 parts by weight whereby the suppository has flexibility and becomes slippery when moistened.

2. The slow-release suppository according to claim 1, wherein the amount of polyvinyl pyrrolidone is from about 30 to about 65 parts by weight, and the amount of water is from about 35 to about 70 parts by weight.

3. The slow-release suppository according to claim 2, wherein the amount of polyvinyl pyrrolidone is from about 30 to 60 parts by weight, and the amount of water is from about 40 to 70 parts by weight.

4. The slow-release suppository according to claim 2, wherein the amount of polyvinyl pyrrolidone is, essentially, 50 parts by weight, and the amount of water is, essentially, 50 parts by weight.

5. The suppository of claim 1 wherein the polyvinyl pyrrolidone has a molecular weight between about 100,000 and 400,000.

6. A slow-release suppository according to claim 1, wherein the therapeutically active ingredient is selected from the group consisting of lignocaine hydrochloride, phenylephrine chloride, betamethasone sodium phosphate, sodium prednisolone metasulphobenzoate, disodium prednisolone phosphate, methylprednisolone sodium succinate, dexamethasone sodium phosphate and hydrocortisone sodium phosphate.

7. The slow-release suppository according to claim 1 wherein the polyvinyl pyrrolidone is a homo-polymer of N-vinyl pyrrolidone.

* * * * *